United States Patent [19]

van der Burg

[11] 4,333,935

[45] Jun. 8, 1982

[54] ANTIANXIETY COMPOSITIONS OF 10-HYDROXY 1,2,3,4,10,14b-HEXAHYDRODIBENZO[c,f-]PYRAZINO-1,2,a AZEPINES AND A METHOD OF USE THEREOF

[75] Inventor: Willem J. van der Burg, Heesch, Netherlands

[73] Assignee: Akzona Incorporated, Asheville, N.C.

[21] Appl. No.: 248,113

[22] Filed: Mar. 27, 1981

Related U.S. Application Data

[63] Continuation of Ser. No. 77,693, Sep. 21, 1979, Pat. No. 4,284,559.

[30] Foreign Application Priority Data

Sep. 26, 1978 [NL] Netherlands ............... 7809726

[51] Int. Cl.³ .................. A61K 31/495; C07D 7/04
[52] U.S. Cl. ......................... 424/250; 260/243.3
[58] Field of Search .................................. 424/250

*Primary Examiner*—David B. Springer
*Attorney, Agent, or Firm*—Robert H. Falk; Charles A. Wendel; Francis W. Young

[57] ABSTRACT

New and pharmacologically useful tetracyclic compounds are disclosed of the formula (I):

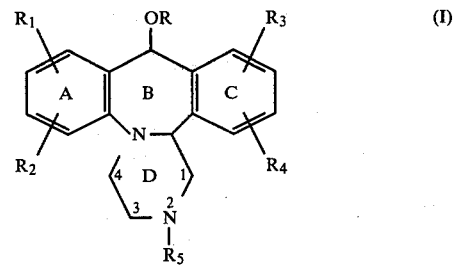

and pharmaceutically acceptable non-toxic salts therefor, wherein:

(a) R is hydrogen, alkyl of one to six carbons, aralkyl of seven to ten carbons, or an acyl group of one to six carbons;

(b) $R_1$, $R_2$, $R_3$ and $R_4$ each represent hydrogen, hydroxy, halogen, alkyl of one to six carbons, alkoxy of one to six carbons, alkythio of one to six carbons, or trifluromethyl; and (c) $R_5$ represents hydrogen or an alkyl group of one to six carbons;

as well as compositions containing these active compounds and methods of using same. The compounds of the instant invention have a remarkable pharmacological profile—one which clearly indicates the presence of anxiolytic properties with little or no sedative activity. The compounds according to the invention thus possess relatively specific anti-anxiety properties.

18 Claims, No Drawings

ANTIANXIETY COMPOSITIONS OF 10-HYDROXY 1,2,3,4,10,14b-HEXAHYDRODIBENZO[c,f]-PYRAZINO-1,2a AZEPINES AND A METHOD OF USE THEREOF

This is a continuation of application Ser. No. 77,693 filed Sept. 21, 1979, now U.S. Pat. No. 4,284,559 issued Aug. 18, 1981.

BACKGROUND TO THE INVENTION

1. Field of the Invention

The invention relates to pharmaceutically active dibenzoazepine-based tetracyclics, or more specifically, dibenzoazepine-based tetracyclics having anxiolytic properties.

2. Description of the Prior Art, and Other Information

Compounds according to general formula I in which the —OR moiety is missing are known, inter alia from U.S. Pat. No. 3,534,041 (which reveals the compound now known as "GB-94"-see below) and its progeny, U.S. Pat. No. 4,025,513 and copending application U.S. Ser. No. 754,216 (not prior art to the instant invention), Canadian Pat. Nos. 965,091, 895,301, all incorporated herein, and application Ser. No. 219,742 (not prior art to the instant invention). See Also U.S. Pat. No. 4,128,641 to Itil (not prior art to the instant invention—issued Dec. 5, 1978), which discloses another use of GB-94, i.e.,

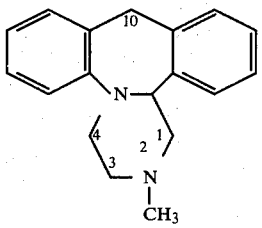

as a neuroleptic agent for schizophrenic patients.

In addition to pronounced antihistamine and antiserotonin activities, the pharmacological profile of these known compounds includes potent anti-depressive and sedative properties.

Also of interest are (1) U.S. Pat. No. 3,701,778 (Van der Burg), which discloses tetracyclics having any of sulfur, oxygen, or $N(C_1-C_6)$ in the 10-position; (2) U.S. Pat. No. 3,917,633 (alkyl substitutes, aminoalkyl, or alkyl aminoalkyl substituents; (3) U.S. Pat. No. 3,959,470, disclosing 3-methyl-8-methoxy- 3H,1,2,5,6-tetrahydropyrazino-[1,2,3]-ab-β-carbolin (anti-depressants); (4) U.S. Pat. No. 3,966,723, teaching a dibenzoazepine-based tetracyclic ring system wherein the 10-position can have a methyl or dimethyl substituent (anti-depressants); (5) U.S. Pat. No. 4,062,848; and (6) British Pat. No. 1,468,632 (no 10-substitution).

SUMMARY OF THE INVENTION

Surprisingly, compounds of the formula:

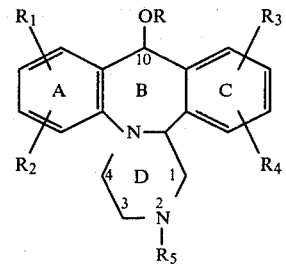

wherein:

(a) R is hydrogen, alkyl of one to six carbons, aralkyl of seven to ten carbons, or an acyl group of one to six carbons;

(b) $R_1$, $R_2$, $R_3$ and $R_4$ each represent hydrogen, hydroxy, halogen, alkyl of one to six carbons, alkoxy of one to six carbons, alkylthio of one to six carbons, or trifluoromethyl; and (c) $R_5$ represents hydrogen or an alkyl group of one to six carbons;

and non-toxic pharmaceutically acceptable salts thereof show a completely different pharmacological profile, one which clearly indicates the presence of anxiolytic properties with little or no sedative activity. The antihistamine and antiserotonin activities of the present compounds are also weak in comparison with the reference substances referred to above. The compounds according to general formula I herein referred to therefore possess significant and specific anti-anxiety properties.

Preferably R is H or $CH_3$, most preferably H. The substituent $R_5$ is preferably alkyl, and in particular methyl. Also, preferably all of $R_1$, $R_2$, $R_3$ and $R_4$ are hydrogen; in the alternative the compounds of formula I are only mono-substituted in one or both phenyl nuclei.

DESCRIPTION OF THE PREFERRED EMBODIMENTS

The compounds according to the invention may be prepared in the way known to those in the art for analogous compounds.

For example, compounds of the general formula I, where R represents hydrogen, may be prepared by direct oxidation of a compound with the general formula:

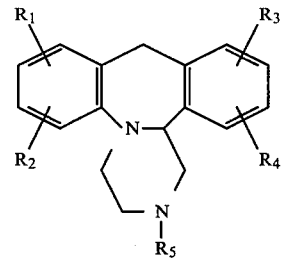

or a pharmaceutically acceptable non-toxic salt thereof, where $R_1$, $R_2$, $R_3$, $R_4$ and $R_5$ possess the meanings given above.

This oxidation is effected by passing oxygen ($O_2$) through a solution of the starting material (II) in a suitable solvent, for example, an appropriate polar solvent such as dimethyl sulphoxide, acetonitrile or dimethylformamide. This oxidation is preferably performed under strongly alkaline conditions obtained by addition of a strong base, such as suitable alkali metal hydroxides or suitable alkali metal alkoxides, to the reaction mixture. See Example I(1).

Suitable alkaline agents which are preferred in this connection are sodium hydroxide in ethanol, potassium or sodium ethoxide in alcohol, and particularly potassium t-butoxide in tertiary butanol. See Example I(1).

The oxidation concerned leads in general to mixtures of the hydroxy compound according to formula I and the corresponding keto-compound. These compounds may be separated by physicochemical separation methods known to those in the art (see Example I(2)), such as fractional crystallization, column chromatography, liquid partition chromatography or preparative thin layer chromatography. The proportions of the two compounds in the mixture depend to a considerable extent on the reaction conditions under which the oxidation is performed. A reaction temperature of about 40° C. or lower generally results in a mixture in which the hydroxy compound according to general formula (I) is the main product. As the temperature increases, progressively, more keto-compound is formed. A temperature of about 20° C. to about 30° C. is preferred.

A second method for the preparation of the compounds (I) herein referred to, in which R represents hydrogen, consists of the reduction of a compound of general formula:

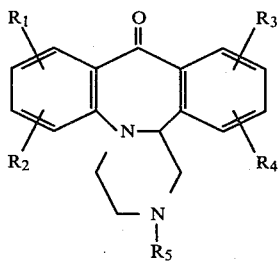

III or a pharmaceutically acceptable non-toxic salt thereof, where $R_1$, $R_2$, $R_3$, $R_4$ and $R_5$ have the meanings previously assigned.

This reduction can be effected in the usual way known to those in the art for this type of reduction, for example, by hydrogenation in the presence of a catalyst, such as platinum oxide, palladium on carbon or Raney nickel, by means of complex metal hydrides, specifically complex aluminium and complex boron hydrides, such as lithium aluminium hydride, sodium or potassium borohydride (see Example III), sodium trimethoxyborohydride and diborane, by means of sodium in alcohol, with the aid of sodium amalgam or zinc in sodium hydroxide or with the aid of aluminium ethoxide or aluminium isopropoxide (Meerwein-Ponndorf reduction). When complex metal hydrides are used, the complex borohydrides are preferred.

The reduction may also be performed electrochemically, with one of the usual metal cathodes such as mercury, lead, zinc or cadmium at a pH of 0 to 14 and a potential with respect to an Ag/AgCl electrode of −0.7 V at pH 0 (the potential increases by −0.06 V per pH unit). See Example VI.

The compounds of general formula (I) where R represents an (ar)alkyl or acyl group are prepared from the compounds (I) where R is hydrogen by means of conventional methods known to those in the art for etherification or esterification.

The ether group, for example, may readily be obtained by reaction of the compound I, where R is hydrogen, with the appropriate alcohol under mildly acid conditions. See Example V.

The compounds according to the invention possess two asymmetric carbon atoms, namely the carbon atoms in the positions 10 and 14b. As a result, two racemic mixtures of formula I are possible, both of which are included amongst the compounds according to the invention. In the one racemic mixture, the cis-mixture, the substituent at the 10-position (the group OR) and the hydrogen atom on the 14b carbon atom have the same orientation, while in the other racemate, the trans-mixture, the substituents are in the opposed orientation. Each racemate further consists of 2 optical antipodes. These optically active cis- or trans-compounds are also included among the compounds according to the invention.

If a racemic starting material of formula (II) or (III) is used, a mixture of the racemic cis-compound according to formula (I) and the racemic trans-compound according to formula (I) is obtained. If, however, use is made of an optically active starting material according to formula (II) or (III), then a mixture of the optically active cis- and trans-compounds according to formula I is obtained.

The ratio of cis to trans compounds in the mixture is dependent to a considerable extent on the conditions under which the reaction is performed. In general, the oxidation described above of the starting material (II) results predominantly in the cis compound. On chemical reduction of compound (III), an approximately 1 to 1 mixture of the cis and trans compounds I is obtained, while the electrochemical reduction gives predominantly trans compound.

The mixture of cis and trans compounds according to formula I can be separated by means of physiochemical separation techniques known to those in the art such as fractional crystallization, column chromatography, liquid partition chromatography, or preparative thin layer chromatography.

The racemic cis or racemic trans compound according to formula I can be resolved into the separate optical antipodes in ways which are common knowledge, for example, with the aid of optically active acids, such as (+) or (−) tartaric acid.

By "pharmaceutically acceptable non-toxic salts" of the compounds according to the invention are meant the pharmaceutically acceptable acid addition salts and quaternary ammonium compounds known to those in the art.

The acid addition salts are obtained by reaction of the free base I with a suitable inorganic or organic acid, such as hydrochloric acid (see Example V), maleic acid, fumaric acid, citric acid, ascorbic acid, etc.

The pharmaceutically acceptable quaternary ammonium compounds, in particular the alkyl ammonium salts of one to four carbons, are prepared by reaction of the free base (I) with an alkyl halide, such as methyl iodide.

The substituent on the nitrogen atom ($R_5$) may also be changed after the reaction noted above, although it is far more preferable that the desired substituent $R_5$ is already present in the starting material according to formula (II) or (III).

The compound I, for example, in which $R_5$ is hydrogen, may be alkylated in a way that is known to those in the art. This alkylation may be effected in a direct way with the aid of an alkyl halide or indirectly by acylation followed by reduction of the N-acyl group.

By an alkyl group in the definition of R, $R_1$, $R_2$, $R_3$, $R_4$ and $R_5$ is understood a branched or straight-chain alkyl group with 1 to 6 carbon atoms, such as methyl, ethyl, propyl, isopropyl, butyl, isobutyl, pentyl or hexyl. The alkyl group with one to four carbon atoms, and in particular the methyl and ethyl group, are preferred.

The alkyl group of the alkoxy and alkylthio group in the definition of $R_1$, $R_2$, $R_3$ and $R_4$ has the same significance.

In the context of this invention, a halogen group is understood to mean fluorine, iodine, chlorine or bromine, whereby the last two halogens named are preferred.

The aralkyl group is preferably a phenylalkyl group with 7 to 10 carbon atoms.

The acyl group in the definition of R is an acyl group derived from an aliphatic carboxylic acid with 1 to 6 carbon atoms, such as acetic acid, propionic acid or butyric acid.

The anxiolytic compounds according to the general formula I may be given either orally, parenterally or rectally, preferably in a daily dosage of about 0.01 to about 10 mg per kg body weight.

When mixed with a pharmaceutical acceptable carrier (i.e., comprising one or more suitable excipients), the compounds may be compressed into solid formulations such as pills, tablets, dragees or suppositories. Optionally mixed with excipients, they may also be processed to give capsules. With the aid of suitable liquids, the compounds may be used in form of solutions, emulsions or suspensions as oral or injection preparations.

Compounds according to the general formula (I) which are preferably used are in general those compounds (I) which possess the cis configuration.

The R-group in the compounds according to the general formula (I) is preferably hydrogen or alkyl, particularly hydrogen or methyl.

The substituent $R_5$ is preferably alkyl, and in particular methyl.

The preferred compounds according to the invention are further unsubstituted ($R_1$, $R_2$, $R_3$ and $R_4$ are hydrogen) or are only mono-substituted in one or both phenyl nuclei.

The invention is exemplified by the following Examples, which should not be construed as limiting the broad embodiments of the invention, but are for illustration purposes only, from which those skilled in the art may depart without going beyond the teachings above or the scope of the appended claims:

The nomenclature and numbering below has been used in the Examples which follow:

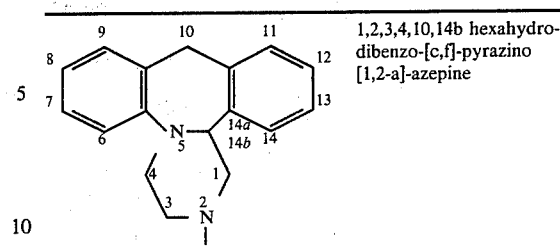

1,2,3,4,10,14b hexahydro-dibenzo-[c,f]-pyrazino[1,2-a]-azepine

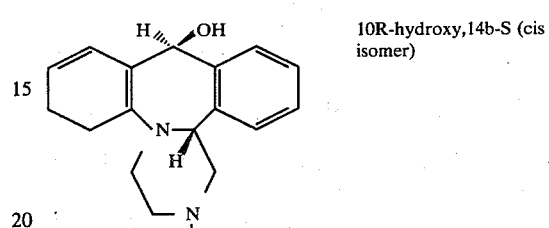

10R-hydroxy,14b-S (cis isomer)

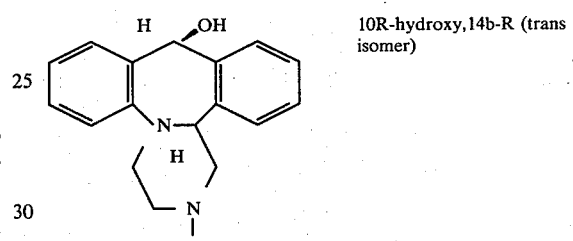

10R-hydroxy,14b-R (trans isomer)

EXAMPLE I

Preparation of 10-hydroxy-2-methyl-1,2,3,4,10,14b-hexahydrodibenzo-[c,f] pyrazino[1,2a]-azepine.

(1) 50 g 2-methyl-1,2,3,4,10,14b-hexahydro-dibenzo[1,2-1]-azepine, 40 g potassium t-butoxide, 1 liter dimethyl sulphoxide and 250 ml t-butanol are mixed and vigorously stirred. Oxygen is passed into this mixture at a temperature of about 30° C., for about 60 minutes. The mixture is subsequently poured into 4 liters water and the resultant precipitate is filtered off and washed with water. After drying in a high vacuum over $P_2O_5$ at 20° C., 50 g of a mixture of the title compound (formula I, here (A)) with the corresponding 10-keto-derivative (B) is obtained. Rf in toluene:ethanol (8:2) on $SiO_2$=0.44 for A and 0.80 for B.

(2) Separation of A and B. 50 g of the mixture (A+B) obtained in (1) is boiled with 250 ml chloroform, cooled and filtered, which provides 36.5 g solid material. This solid is boiled with a mixture of 800 ml methanol and 50 ml dimethyl sulphoxide. Cooling results in 29.8 g compound A in pure form. Melting point 222°–224° C.; Rf in toluene-ethanol (8:2)=0.44 on $SiO_2$. Stereo-configuration shows the cis compound (10R, 14b-S).

The combined filtrates are evaporated to dryness and the residue is chromatographed on 1 kg silica gel with chloroform as eluent. The product obtained is crystallized from 300 ml methanol, giving 7 g compound B in pure form. Melting point: 153°–156° C.

EXAMPLE II

The following compounds are prepared in a corresponding way:

8-chloro-10-hydroxy-2-methyl-1,2,3,4,10,14b-hexahydrodibenzo[c,f] pyrazino-azepine; (cis configuration), melting point 218°–220° C.

2,7-dimethyl-10-hydroxy-1,2,3,4,10,14b-hexahydrodibenzo[c,f]-pyrazino[1,2-a]azepine;

2,13-dimethyl-10-hydroxy-1,2,3,4,10,14b-hexahydrodibenzo[c,f]-pyrazino[1,2-a]azepine;

8,10-dihydroxy-2-methyl-1,2,3,4,10,14b-hexahydrodibenzo[c,f]-pyraxino[1,2-a]azepine, (cis configuration), Rf in ethanol:acetone (9:1) =0,40 on $SiO_2$;

10-hydroxy-14-methoxy-2-methyl-1,2,3,4,10,14b-hexahydrodibenzo[c,f]pyrazino[1,2-a]azepine;

10-hydroxy-1,2,3,4,10,14b-hexahydrodibenzo[c,f]pyrazino[1,2-a]azepine, (cis configuration), Rf in ethanol:acetone (9:1) =0.43 on $SiO_2$, m.p. 217° C.

EXAMPLE III 10-hydroxy-2-methyl-1,2,3,4,10,14b-hexahydrodibenzo[c,f]pyrazino[1,2-a]azepine 1 g 10-oxo-2-methyl-1,2,3,4,10,14b-hexahydrodibenzo [c,f]pyrazino[1,2-a]azepine is dissolved in 25 ml ethanol, after which 1 g sodium borohydride is added and the mixture is heated at 80° C. for about 1 hour. It is subsequently cooled to about 20° C., after which 25 ml 2 N acetic acid is added dropwise. The mixture is poured into 200 ml water and extracted with methylene chloride. The extracts are dried and evaporated to dryness. The residue is crystallized from methanol, giving 200 ml pure cis product (1OR, 14b-S) of melting point 222°–225° C. After evaporation to dryness and chromatography on silica gel, 300 mg trans product (1OR, 14R) of melting point 137°–138° C. is obtained, Rf in toluene:ethanol (8:2)=0.38 on $SiO_2$.

EXAMPLE IV

The compound 8-chloro-2-methyl-10-oxo-1,2,3,4,10,14b-hexahydrodibenzo[c,f]pyrazino[1,2-a]azepine (melting point 188°–190° C.) is reduced in a way corresponding to that described in Example III.

Melting point of 8-chloro-2-methyl-1,2,3,4,10,14b-hexahydrodibenzo[c,f]pyrazino[1,2-a]azepine: 218°–220° (cis).

EXAMPLE V

Cis-10-methoxy-2-methyl-1,2,3,4,10,14b-hexahydrodibenzo[c,f]pyrazino[1,2-a]azepine hydrochloride 1 g cis-10-hydroxy-2-methyl-1,2,3,4,10,14b-hexahydrodibenzo[c,f]pyrazino[1,2a]azepine is suspended in 25 ml methanol, after which 2 ml of a saturated solution of HCl in methanol is added and the mixture is boiled for about 1 hour with exclusion of moisture. The solution is evaporated to dryness under vacuum and the residue is crystallized from methanol. Yield 300 mg. Melting point of the HCl salt: 247°–251° C.; melting point free base 182°–184° C.

The cis-10-ethoxy compound is prepared in a corresponding fashion. Melting point 149°–150° C.

EXAMPLE VI 10-hydroxy-2-methyl-1,2,3,4,10,14b-hexahydrodibenzo[c,f]pyrazino[1,2-a]azepine 5 g 10-oxo-2-methyl-1,2,3,4,10,14b-hexahydrodibenzo [c,f]pyrazino[1,2-a]azepine is dissolved in 600 ml methanol/0.2 N NaOH (7:3) and reduced electrochemically by applying a current with a density of about 8 mA/cm² with mercury as cathode for about 5 hours. The solution is reduced in bulk until a precipitate forms, diluted with 200 ml water and shaken with ether. The ether extract, on evaporation, gives 5 g of a residue which consists of a mixture of the cis and trans title product (ratio about 1:4). Chromatography on silica gel gives 3.7 g of the trans isomer, melting point 137°–138° C.; Rf in toluene:acetone (6:4)=0.25 on $SiO_2$.

It is claimed as the invention:

1. A pharmaceutical composition for treating anxiety in a patient, comprising:
   (a) a pharmaceutically effective anxiety reducing amount of a compound of the formula:

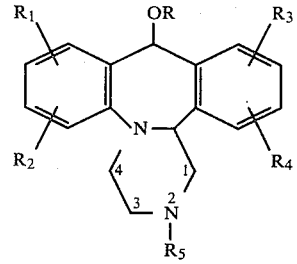

or a pharmaceutically effective non-toxic salt thereof, wherein:
   (a) R is hydrogen, alkyl of one to six carbons, aralkyl of seven to ten carbons, or carboxylic acyl group of one to six carbons;
   (b) $R_1$, $R_2$, $R_3$ and $R_4$ each represent hydrogen, hydroxy, halogen, alkyl of one to six carbons, alkoxy of one to six carbons, alkylthio of one to six carbons, or trifluromethyl; and
   (c) $R_5$ represents hydrogen or an alkyl groups of one to six carbons; and
   (B) a pharmaceutically effective carrier.

2. A composition according to claim 1, wherein R is H or alkyl of one to six carbons.

3. A composition according to claim 1, wherein R is H or $CH_3$.

4. A composition according to claim 1, wherein $R_5$ is $CH_3$.

5. A composition according to claim 1, wherein at least three of $R_1$, $R_2$, $R_3$ and $R_4$ are H.

6. A composition according to claim 1, wherein one of $R_1$, $R_2$, $R_3$ and $R_4$ is Cl, OH, $CH_3$ or $CH_3O$.

7. A composition according to claim 1, wherein R is H, $R_1$ is H, $R_2$ is H, $R_3$ is H, and $R_4$ is H, and $R_5$ is $CH_3$.

8. A composition according to claim 1, wherein R is H, $R_1$ is Cl, $R_2$ is H, $R_3$ is H, $R_4$ is H, and $R_5$ is $CH_3$.

9. A composition according to claim 1, wherein R is H, $R_1$ is H, $R_2$ is $CH_3$, $R_3$ is H, $R_4$ is H, and $R_5$ is $CH_3$.

10. A composition according to claim 1, wherein R is H, $R_1$ is H, $R_2$ is H, $R_3$ is H, $R_4$ is $CH_3$, and $R_5$ is $CH_3$.

11. A composition according to claim 1, wherein R is H, $R_1$ is OH, $R_2$ is H, $R_3$ is H, $R_4$ is H, and $R_5$ is $CH_3$.

12. A composition according to claim 1, wherein R is H, $R_1$ is H, $R_2$ is H, $R_3$ is H, $R_4$ is $CH_3O$, and $R_5$ is $CH_3$.

13. A composition according to claim 1, wherein R is H, $R_1$ is H, $R_2$ is H, $R_3$ is H, $R_4$ is H, and $R_5$ is H.

14. A composition according to claim 1, wherein R is $CH_3$, $R_1$ is H, $R_2$ is H, $R_3$ is H, $R_4$ is H, and $R_5$ is $CH_3$.

15. A composition according to claim 1, wherein R is $C_2H_5$, $R_1$ is H, $R_2$ is H, $R_3$ is H, $R_4$ is H, and $R_5$ is $CH_3$.

16. A method for treating anxiety in humans which comprises administering to a human
   a pharmaceutically effective anxiety reducing amount of a compound of the formula:

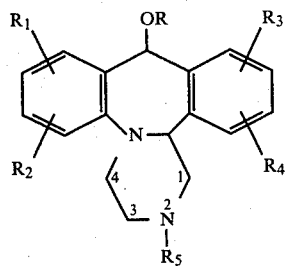

or a pharmaceutically effective non-toxic salt thereof, wherein:

(a) R is hydrogen, alkyl of one to six carbons, aralkyl of seven to ten carbons, or a carboxylic acyl group of one to six carbons;
(b) $R_1$, $R_2$, $R_3$, and $R_4$ each represent hydrogen, hydroxy, halogen, alkyl of one to six carbons, alkoxy of one to six carbons, alkylthio of one to six carbons, or trifluromethyl; and
(c) $R_5$ represents hydrogen or an alkyl group of one to six carbons.

17. The method of claim 16, wherein the compound is administered orally.

18. The method of claim 16, wherein the compound is administered in a daily dosage of about 0.01 to about 10 mg per kg of body weight.

* * * * *